United States Patent
Brunner et al.

(10) Patent No.: US 10,278,643 B2
(45) Date of Patent: May 7, 2019

(54) BELT FOR ELECTRO IMPEDANCE MEASUREMENT AND METHOD USING SUCH BELT

(71) Applicant: SWISSTOM AG, Landquart (CH)

(72) Inventors: Josef X. Brunner, Chur (CH); Stephan H. Bohm, Lauenburg/Elbe (DE)

(73) Assignee: SWISSTOM AG (CH)

( * ) Notice: Subject to any disclaimer, the term of this patent is extended or adjusted under 35 U.S.C. 154(b) by 1235 days.

(21) Appl. No.: 14/375,069

(22) PCT Filed: Jan. 28, 2013

(86) PCT No.: PCT/CH2013/000016
§ 371 (c)(1),
(2) Date: Jul. 28, 2014

(87) PCT Pub. No.: WO2013/110207
PCT Pub. Date: Aug. 1, 2013

(65) Prior Publication Data
US 2015/0038823 A1    Feb. 5, 2015

(30) Foreign Application Priority Data
Jan. 27, 2012 (CH) ........................ 116/12

(51) Int. Cl.
*A61B 5/04* (2006.01)
*A61B 5/00* (2006.01)
(Continued)

(52) U.S. Cl.
CPC .......... *A61B 5/6805* (2013.01); *A61B 5/0531* (2013.01); *A61B 5/0536* (2013.01);
(Continued)

(58) Field of Classification Search
CPC . A61B 5/04085; A61B 5/6831; A61B 5/6804; A61B 5/0006; A61B 5/6805;
(Continued)

(56) References Cited

U.S. PATENT DOCUMENTS 5,353,793 A    10/1994   Bornn
5,443,494 A *  8/1995   Paolizzi ............... A61B 5/6831
                                                    600/390
(Continued)

FOREIGN PATENT DOCUMENTS

EP    2072009 A1   6/2009
GB    2400915 B   10/2004

OTHER PUBLICATIONS

Zhao Zhanqi et al.: PEEP titration guided by ventilation homogeneity: a feasibility study using electrical impedance tomography, Critical Care, Biomed Central Ltd., London, GB, vol. 14, No. 1, Jan. 30, 2010.

(Continued)

*Primary Examiner* — Joseph Stoklosa
*Assistant Examiner* — Brian M Antiskay
(74) *Attorney, Agent, or Firm* — Morriss O'Bryant Compagni Cannon, PLLC

(57) ABSTRACT

An electro impedance measuring belt for placing electrodes around the thorax of a patient comprises an array of a plurality of spaced apart electrodes, and a support structure, on which the electrodes are arranged. The support structure with the electrode array comprises two angulated legs on which the electrodes are lined up, the two legs spread out from an apex at an angle, such that, when the belt is put around the thorax of a patient, the array of electrodes extends from the back of the patient, where the apex of fee angulated legs is to be located, essentially parallel to the ribs to the lower part of the breastbone of the patient.

20 Claims, 11 Drawing Sheets

(51) Int. Cl.
   *A61B 5/053* (2006.01)
   *A61B 5/08* (2006.01)
   *F24C 15/20* (2006.01)
   *A61B 5/0295* (2006.01)

(52) U.S. Cl.
   CPC ........ *A61B 5/0809* (2013.01); *F24C 15/2035* (2013.01); *A61B 5/0295* (2013.01); *A61B 5/0535* (2013.01)

(58) Field of Classification Search
   CPC . A61B 5/02438; A61B 5/0478; A61B 5/0245; A61B 5/0402; A61B 5/053; A61B 5/0531
   USPC ........ 600/372, 382, 384, 386, 388, 390–393
   See application file for complete search history.

(56) References Cited

U.S. PATENT DOCUMENTS

| | | | | |
|---|---|---|---|---|
| 5,445,149 | A * | 8/1995 | Rotolo | A61B 5/04085 600/382 |
| 5,626,146 | A | 5/1997 | Barber et al. | |
| 5,871,534 | A * | 2/1999 | Messick | A61N 1/0452 600/382 |
| 6,065,154 | A * | 5/2000 | Hulings | A61N 1/0484 2/102 |
| 6,847,836 | B1 * | 1/2005 | Sujdak | A61B 5/04085 600/382 |
| 8,019,402 | B1 | 9/2011 | Kryzpow | |
| 8,818,478 | B2 * | 8/2014 | Scheffler | A41D 1/002 600/388 |
| 2004/0236202 | A1 | 11/2004 | Burton | |
| 2006/0135863 | A1 * | 6/2006 | Birnbaum | A61B 5/0002 600/388 |
| 2006/0142654 | A1 * | 6/2006 | Rytky | A61B 5/0245 600/388 |
| 2008/0114232 | A1 * | 5/2008 | Gazit | A61B 5/6831 600/390 |
| 2008/0287769 | A1 * | 11/2008 | Kurzweil | A61B 5/0408 600/388 |
| 2008/0287770 | A1 | 11/2008 | Kurzweil | |
| 2009/0084674 | A1 | 4/2009 | Holzhacker et al. | |
| 2010/0198043 | A1 * | 8/2010 | Holzer | A41D 13/1281 600/388 |
| 2013/0053674 | A1 * | 2/2013 | Volker | A61B 5/04085 600/389 |

OTHER PUBLICATIONS

Costa, Eduardo L.V., (Feb. 2009) "Electrical impedance tomography." Current Opinion in Critical Care 15 (1):18-24. Lippincott Williams & Wilkins, United States.

* cited by examiner

BELT FOR ELECTRO IMPEDANCE MEASUREMENT AND METHOD USING SUCH BELT

CROSS-REFERENCE TO RELATED APPLICATIONS

This application is a national phase entry under 35 U.S.C. § 371 of PCT/CH2013/000016 filed on Jan. 28, 2013, which claims priority to Swiss Patent Application 116/12 filed on Jan. 27, 2012, the entirety of each of which is incorporated by this reference.

TECHNICAL FIELD OF THE INVENTION

The field of the invention relates to an electro impedance measurement belt and a method of electro impedance measurement using such a belt.

BACKGROUND OF THE INVENTION

Electrical impedance tomography (EIT) is a non-invasive imaging technique used to investigate and measure regional lung ventilation and perfusion (flow of blood) in humans and animals. In contrast to conventional methods, EIT does not require the patient to breathe through a tube or sensor, does not apply ionizing X-rays and can be used for extended periods, say 24 hours or even longer. EIT can be used continuously and is therefore suited for monitoring treatment effects in real time and over time, EIT was first used to monitor respiratory function in 1983 and remains the only bedside method that allows continuous, non-invasive measurements of regional changes in lung volume, blood flow, and cardiac activity. More details of this technique can be found in "Electrical impedance tomography" by Costa E. L., Lima R. G, and Amato M. B. in Curr Opin Crit Care, February 2009, 15(1), p. 18-24.

Traditionally electrodes used for electro impedance measurements and in particular electro impedance tomography (EIT) are placed individually on the thoracic surface to form an electrode plane. Such individual electrodes are cumbersome to handle and are bound to be dislocated with patient movement. In order to overcome the above problem, belts (or belt-like structures) have been designed on which electrodes are mounted. The conventional belt is placed around the chest thereby forming a transverse EIT plane. For example document US 2009/0084674 A1 discloses an electrode assembly for electrical impedance tomography comprising a plurality of different electrode modules. Each module contains a support strap carrying a predetermined number of electrodes with a distance between each two consecutive electrodes predetermined as a function of a specific operational pattern. Also here the belt is placed around the chest, thereby forming a transverse EIT plane.

While such conventional belts solve the problem of electrode handling, despite the fact that they are often elastic, they restrict the breathing of the patient particularly by preventing the ribs from lifting upwards during respiration. Conventionally the belt is placed at an angle with respect to the extension of the ribs around the chest. As this angle is bigger than zero, there is a force preventing the free movement of the ribs. Consequently, to some extent the natural movement of the chest during respiration is restricted.

Such external restriction of the chest movement during respiration however can prevent optimal ventilation of a patient or produce artifacts during EIT examination.

In EIT, as disclosed by U.S. Pat. No. 5,626,146, a plurality of electrodes, typically 8 to 32, are arranged on the surface of the body to be examined. A control unit ensures that an electrical signal, for example a current is applied to one or several pairs of electrodes on the skin to establish an electrical field, which in turn is measured by the other electrodes.

Typically the electrodes are arranged on the surface of the body to be examined in such a way that they surround the body girth. Conveniently a belt structure supports the electrodes and is located about the chest of the patient in a transverse plane. Such positions have been shown e.g. in patent application EP 1 000 580 A1.

A good contact of the electrodes with the body of a test subject is essential to the EIT method. In order to establish good contact electrode belts have been proposed which are elastic, see e.g. patent specification GB 2 400 915 B. An elastic belt is under a certain pretension, as a result of which a radial force component acts as a pressing force on the electrodes and also on the test subject's body. To a certain extent such forces impede normal chest movement and extension during breathing. Due to the elasticity of the belt special provisions for electrode supply lines need to be made, such as folding supply lines in zigzag or meandering manner, to compensate for expansion of the belt material Moreover, in order to ensure further improved electrode contact also at body areas with inward curvatures, air-tight elements filled with air, liquid or gel are placed at the back of the electrodes.

Patent application US 2004/0236202 A1 proposes an alternative expandable electrode belt made of material that is flexible and bendable, yet inelastic. Hereby waves or bends in the belt allow the belt to be extended, while the electrodes remain spaced apart equidistantly as the strap extends—either during application onto or respiration by a patient. Physically, such belt will buckle as it is extended, which is disadvantageous where the test subject is a patient lying in bed.

Other belt-type garments are designed for the purpose of carrying sensors. For example, patent application US 2008/0287770 A1 discloses a garment for ambulatory, physiological monitoring of a patient comprising a belt, having first and second end portion with closures at the end portions to wrap around a user's chest, a pair of shoulder strap portions, and a back portion, with at least one of the belt portions, the strap portions and the back portion having an accommodation for carrying one or more singular sensors, such as an ECG sensor. Another example is given in patent specification U.S. Pat. No. 5,353,793 A. Here is disclosed another harness-like garment enabling measurements of physiological parameters of a patient. This garment comprises a chest band, an optional shoulder band(s), and an optional abdominal band that can house respiration, pulse and ECG sensors for impedance pneumography. The garment is stretchable and. all bands are worn on the body under tension. In a presented example several electrodes are arranged on the front of the shoulder band(s) and at some parts of the chest hand. The chest band apparently forms a transverse sensor plane.

Advantages of the Invention

It is an advantage of the present invention to provide a device and method for allowing an optimal electro impedance measurement representation, in particular electro impedance tomographic representation of the lung and heart. Ideally, also the movement of the diaphragm should be traceable.

Furthermore, it is an advantage of the present invention to perform electro impedance imaging, in particular EIT imaging, without at the same time obstructing the thoracic respiration movement with the electro impedance equipment respectively the EIT equipment.

It is a further advantage of the present invention to provide a device designed and manufactured in such a way as to guarantee compatibility between the materials of the device and biological tissues, cells and body fluids, taking account of the intended purpose of the device and for a sufficient duration of use.

Moreover it is an advantage of the present invention to provide a non-obstructive electro impedance measuring electrode belt design, in particular to provide a n onobstructive EIT electrode belt design.

It is an advantage of the present invention to provide a new and improved EIT imaging electrode belt and method of EIT imaging.

It is an advantage of the present invention to provide a new and improved electro impedance measuring belt and method of electro impedance imaging.

It is another advantage to provide a cost efficient and low cost EIT belt and EIT belt manufacturing method so that it can be disposed, after use.

SUMMARY OF THE INVENTION

According to present invention the inventive electro impedance measuring electrode belt (herein also called electrode belt) is designed to follow the anatomy of the ribs. Thus, the electrode array (array of lined up electrodes) of the belt follows the space between two ribs (intercostal space) or a rib from the upper dorsal thorax towards the lower front at the sternum. The design of the electro impedance measuring belt electrode is such that the belt and therefore the electrodes are placed in such a way that the array's longitudinal extension follows the extension of the ribs at both sides of the thorax. In one embodiment an essentially transverse center piece of the electrode impedance measuring electrode belt lying across the spine acts as a hinge-like fixture of the right and left electrode impedance measuring belt extensions alongside the ribs as well as their electrical connection. Next to the mechanical advantages with regards to the breathing there are also at least two other key advantages of such a belt design, The electro impedance measuring electrode belt is an electro impedance tomography belt (EIT-belt) and the electro impedance measuring method is an electro impedance tomography method (EIT-method). The inventive electro impedance measuring belt may be used for any impedance measurements and measurement methods.

The oblique application of the electrode belt on the thorax following the ribs leads to a better representation of the thoracic cavity, including heart and lungs, as more of their tissue can be subjected to EIT measurements. By using the oblique belt design, extreme transverse traditional electrode positions such as a low belt position below the breast (showing little lung and considerable amounts of liver tissue) or a high belt position above the breast (where very little or no more heart tissue can be detected and where the kings become small) can be avoided reliably.

As the ribs are neither distensible nor elastic or stretchable, a belt following the ribs closely does not need to be stretchable, elastic, extendable, distensible or alike. All such a belt needs to be is flexible and/or curved so that it can follow the ribs along the body contour in order to adapt to a patient's anatomy.

Advantageously, such electrode belt or electrode band, respectively, can be made of non-distensible, non-stretchable, non extendable and non-elastic but flexible materials, such as e.g. flexible printed electronic circuit boards. Such electrode belt can be produced in a cheaper and cost efficient way. This inventive type of electrode contacting is technically less challenging and less delicate.

In consequence, EIT measuring belts designed according to the above principles are more comfortable to wear and cheap to produce while achieving more representative EIT images.

The advantages of the invention can be achieved when a support structure with an array of a plurality of electrodes comprises two angulated legs such that, when the belt is applied around the thorax of a patient, the array of a plurality of electrodes extends from the back of the patient, in particular form the spinal column, where the apex of the angulated legs or the transverse part connecting them are to be located, essentially parallel to the ribs (i.e. along the extension of the ribs) to the lower part of the breastbone (sternum) of the patient. This has the advantage that—in contrast to the prior art—no elastic or extendable electrode belt is required. This allows a reduction of the manufacturing costs of the electrode belt. In addition, by placing the electrodes along the ribs or in the intercostal space between two neighboring ribs an even more meaningful EIT image can be obtained.

Thus, the inventive electro impedance measuring belt (herein also called electrode belt) for placing electrodes around the thorax of a patient comprises, an array of a plurality of spaced apart electrodes, and a support structure, on which the electrodes are arranged, wherein the support structure with the electrode array comprises two angulated legs on which the electrodes are lined up, the two legs spread out from an apex at an angle, such that, when the belt is put around the thorax of a patient, the array of electrodes extends from the back of the patient, where the apex of the angulated legs or the transverse part connecting them are to be located, essentially parallel to the ribs to the lower part of the breastbone of the patient. The apex is situated at tine back part of the belt and from the apex the legs spread out in a descending manner, i.e. obliquely downwards, towards the front part, so that an angle opens up between the two legs. Consequently, e.g. when worn by a patient or another test person, the apex of the two angulated legs or the transverse part connecting them are arranged on the spinal column and then following the oblique orientation of the ribs. The angle (a) formed between the legs may be between 80 and 170 degree, between 90 and 160 degree, between 110 and 150 degree or between 120 and 140 degree.

According to an embodiment of the invention where the two legs are connected by a transverse middle part, the angle (β) between the longitudinal axis of the transverse middle part and the longitudinal axis of the legs may be between 5 and 50 degree, between 10 and 45 degree, between 15 and 35 degree or between 20 and 30 degree. The provision of a transverse extending middle part has the advantage that two electrodes can be placed just near the spinal column and in a region where valuable diagnostic information can be gained.

Advantageously, the legs are designed as straps comprising first fastening means at their ends for correcting their ends together. This design has the advantage that the belt can relatively easily be mounted on bedridden patients.

In the following the combination of support structure and electrodes may also be called electrode band, since in one embodiment said combination of support structure and electrodes advantageously is designed as a band.

According to another embodiment of the invention additionally an attachment structure or attachment means is provided for holding the support structure with the array of electrodes in position, so that essentially no relative movement between the electrodes and the body of the patient occurs during breathing. Due to the attachment structure it is no longer necessary to resort to a stretchable electrode belt. Thus, the electrode belt may be inelastic. At the same time, the electrode belt is bendable for better wearability. A characteristic of the attachment means or attachment structure is that it allows positioning of the electrodes of the array with respect to the craniocaudal axis at the back of a body at a more elevated level, which is closer to the head-end than at its front.

Different embodiments for allowing to hold the support structure and electrodes are feasible, The attachment structure can be designed to be connected on the one hand directly or indirectly to the body of the patient and on the other hand to the support structure. Alternatively, the attachment structure could be a separate belt wrapped around the body and connected to the lower part of the support structure (e.g. an electrode band) near or at its lowest point, i.e. in the region of the breastbone. In order to allow for the expansion of the thorax during breathing, the attachment structure is at least partially elastic.

Different designs of the attachment structure are feasible without deviating from the gist of the invention. For instance, the attachment structure can be a kind of a harness adapted to hold the support structure in position. The attachment structure can comprise one or more suspenders designed to be put over the shoulders of a patient. It can be designed as a kind of harness, a vest-like, clothing or vest adapted to position and carry said support structure with the electrode array. The vest-like clothing or vest may be manufactured at least partially from an elastic textile in order to allow movement of the thorax during breathing. For example, elastic textiles comprise woven, non-woven, knitted or other kind of textiles. However, alternatively the attachment structure may be inelastic (i.e. for example made of a non-elastic material). The attachment structure and the support structure can be releasably or permanently connected with each other. Alternatively or in addition, the attachment structure may comprise adhesive elements restricting relative movement between electrodes respectively the electrode carrying support structure and a patient.

Advantageously the attachment means or structure allow positioning of the electrodes of the array with respect to the craniocaudal axis at the back of a body at a more elevated level (which is closer to the head-end) than at its front.

The attachment structure comprises at least a first strap or suspender for leading over at least one shoulder and/or around the neck (e.g. from the dorsal part to the ventral part of the belt), which serves to position the dorsal part of the belt at the desired position, and optionally a second strap connected to at least the ventral part of the belt and leading around the torso and/or past the crotch, which serves to position the ventral part of the belt at the desired position and In particular inhibiting the ventral part of the belt from slipping upwards or cranially on the chest region. Advantageously, said optional second straps may be at least partially elastic.

The electrode array and its support structure form an integral element comprising at least two layers, wherein a first layer comprises a skin-contacting cloth with electrically conducting pathways for establishing contact between the skin and the electrodes and a second layer comprises an electronic circuit board. Optionally, the electronic circuit board has also the function of the support structure, defines a plurality of electrode positions, and comprises supply lines, control lines and/or data lines for connecting tire electrodes with an analyzing and control instrument.

Optionally, the electronic circuit board is placed in a tube-like structure formed by the skin-contacting cloth with electrically conducting pathways for establishing contact between the skin and the electrodes. The tube-like structure may be an integral part of the attachment structure, Advantageously, the electrode array (or rather the support structure or electrode band), when attached to the attachment structure, in particular to the harness or vest-like clothing, and spread out flat, shows a bent or curved shape, or an upside down v-like shape for allowing alignment with the rib inclination.

For the purpose of ensuring non-slip fitting of the belt, the attachment structure can comprise an enlarged contact area particularly in the lower dorsal area.

It is possible that the support structure of the array is essentially non-stretchable and/or non-elastic, in particular e.g. an electronic circuit board is usually non-stretchable and non-elastic.

However the support structure of the array may be flexible and bendable which is advantageous for the purpose of fitting the belt on and around the thorax of a patient.

The material of the support structure, in particular of the harness or vest-like clothing, may be breathable and/or at least partially elastic.

Such electro impedance measuring belt can be designed for single use.

The advantages of the invention can be achieved by an electro impedance measuring method comprising the application of an electrode impedance measuring belt which belt comprises an array of electrodes arranged in a spaced apart manner along the longitudinal extension of the belt, wherein the array of electrodes is placed essentially along the ribs or in the intercostal region of two neighboring ribs around the thorax of a human being. For the purpose of placing an array of electrodes essentially along the ribs or in the intercostal region of two neighboring ribs around the thorax of a human being an electro impedance measuring belt as described herein may be used. Such belt comprises an array of a plurality of lined up, spaced apart (evenly spaced apart) electrodes. The array (i.e. the line) in which the electrodes are lined up comprises two straights connected via a bend; wherein said bend comprises an angle (a) advantageously between 80 and 170 degree, between 90 and 160 degree, between 110 and 150 degree or between 120 and 140 degree.

The array of a plurality of electrodes defines an oblique oval electrode plane at an angle ($\gamma$) with respect to the transverse plane (i.e. transverse body plane 55) due to inclination about a transverse axis running from the left to the right side of a body. Said angle (y) with respect to the transverse plane approximately corresponds to the rib inclination with respect to the dorsoventral axis. Moreover, said angle ($\gamma$) comprises approximately 20 to 60 degree. If the electrode impedance measuring belt is adjusted, the array of electrodes follows one specific rib on one side of the body and the corresponding specific rib on the other side of the body. Consequently, the array of electrodes with respect to the craniocaudal axis surrounds the body posteriorly at a higher level than anteriorly. The electrodes are positioned between the $4^{th}$ and the 7) rib. Alternatively the electrodes are positioned at the level of a specific intercostal space, between the 4th and 5th or between the 5th and 6th rib, or between the 6th and 7th rib. It was found that EIT image data measured in these positions (i.e. in these oblique body planes) allow for an optimal analysis of the conditions of lung and heart.

The inventive electro impedance measuring method delivers particularly useful results for the purpose of further lung diagnosis, if the array of electrodes comprises at least 8 electrodes, 16 electrodes, or at least 30 electrodes, and further spans in an evenly spaced apart manner at least 70%, or at least 80%, of the circumferential length of a patient in its oblique thoracic measurement plane.

From above follows that an electro impedance belt according to present invention may be used for performing electro impedance measurements and/or for performing electro impedance imaging methods.

BRIEF DESCRIPTION OF THE DRAWINGS

Other advantages of the present invention will become apparent to those skilled in the art upon reading the following detailed description of illustrated embodiments, in conjunction with the accompanying drawings. The invention will be described in detail hereinafter with reference to the figures, in which, schematically.

DETAILED DESCRIPTION OF THE ILLUSTRATED EMBODIMENTS

Figure 1:
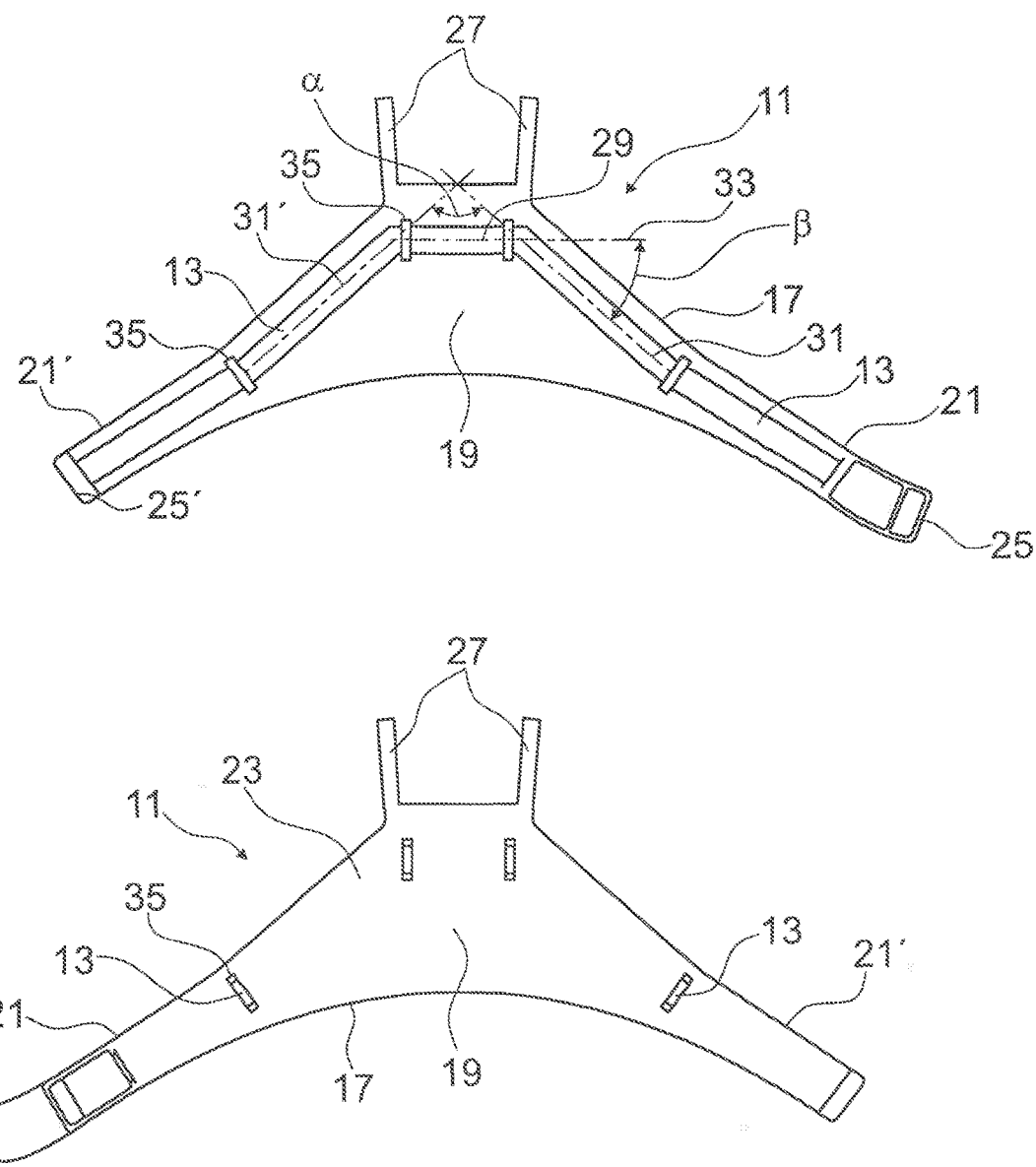
FIG. 1 shows a first embodiment of the inventive EIT measuring belt comprising a support structure and an array of electrodes forming together an electrode band and an attachment structure connected with the electrode band
 a) view from the inside and
 b) view from the outside.

The EIT measuring belt 11 of FIGS. 1 to 4 comprises a support structure 13 carrying a plurality of electrodes 15 and a attachment structure 17 to which the support structure 13 is affixed. The support structure 13 with the electrodes 15 thereby forms an electrode band 16. The electrodes are connectable to an EIT measurement module (not shown here). The characteristic of the inventive EIT measuring belt is that it is designed to be wrapped around the thorax of a patient in an oblique angle so that the plurality of electrodes extends essentially parallel to the ribs of a patient (i.e. along the longitudinal extension of the ribs or their intercostal space). Thus, the electrodes lined up in an array; which array essentially can be fitted to a patient in a parallel row along tire longitudinal extension of the ribs or their intercostal space, in other words, the electrode band 16 is designed such that it can be placed around the chest at an angle to the transverse plane of the human body. Deviation from the transverse plane is such that the angle between an oblique plane; which is defined by the plurality of the electrodes, and the longitudinal extension of the ribs or their intercostal space around tire chest (the angle between said oblique plane and one of the central ribs, such as e.g. the $4^{th}$, $5^{th}$, $6^{th}$, or $7^{th}$ rib) is approximately zero.

This novel electrode arrangement means that the EIT image now approximately corresponds to a larger cross-sectional area of the human thorax due to a larger anterior-posterior dimension compared to a traditional transverse cross-section as it is the case with conventional EIT measurements performed with EIT electrodes arranged in a transverse plane, Said conventional EIT measuring devices are wrapped around the thorax at essentially the same height of the body, usually at the lower section of the breastbone, so that the EIT image corresponds essentially to a cross-section extending orthogonally or transverse to the longitudinal axis of the body.

The advantage of the inventive HIT measuring belt is that the support structure 13 for the electrodes 15 can now be a non-stretchable band, since it is designed to extend parallel to the ribs. A further advantage is that also upper lung sections can be made visible. In order that the support structure 13 with the electrodes 15 is kept in place on the thorax during breathing, the attachment structure 17 is provided. The attachment structure 17 can be a kind of harness 19 as shown in FIG. 1. It comprises two straps 21 and 21 extending from a middle portion 23 having fixation means 25 and 25', e.g. VELCRO hook and loop fasteners, at their ends allowing to connect their ends together. The middle portion 23 is further equipped with one or two suspenders 27, which are to be put over the shoulders of a patient. The straps 21, 21' comprise at least partially a stretchable portion, which allows expansion due to the breathing of the patient. FIG. 1 shows an inside view (upper image) and an outside view (lower image) of the harness 19.

The support structure 1.3 with the electrodes 15 comprises a middle part 29, from which a leg 31, 31' extends on either side at an angle β of about between 5 to 50 degree with respect to the transverse right to left axis 33 of the middle part 29. Although not compulsory, the support structure 13 is releasably or permanently affixed to the attachment structure 17. For this purpose, loops 35 (e.g. cut out from the harness material as shown in FIG. 1), glue, adhesive tape or VELCRO hook and loop fasteners can be provided for affixing the electrode band 16 to the attachment structure. According to one embodiment angle α is between 110 to 130 degree, and β (which equals to 90−α/2) is between 25 and 35 degree.

According to the embodiment shown in FIGS. 1 to 4 the electrode band 16 is received in an envelope 37 or 37' of an electrically conducting material. Said electrically conducting material functions as interface between the electrically conducting electrode surface and the skin of a patient. The electrically conducting material is subject of the co-pending published application WO 2012/006753 A1 whose content is hereby incorporated by reference.

As shown in FIGS. 2, 3, 5 and 6, the electrodes are lined, up in spaced apart manner. Advantageously the gaps between successive electrodes are approximately equidistant.

Figure 4:
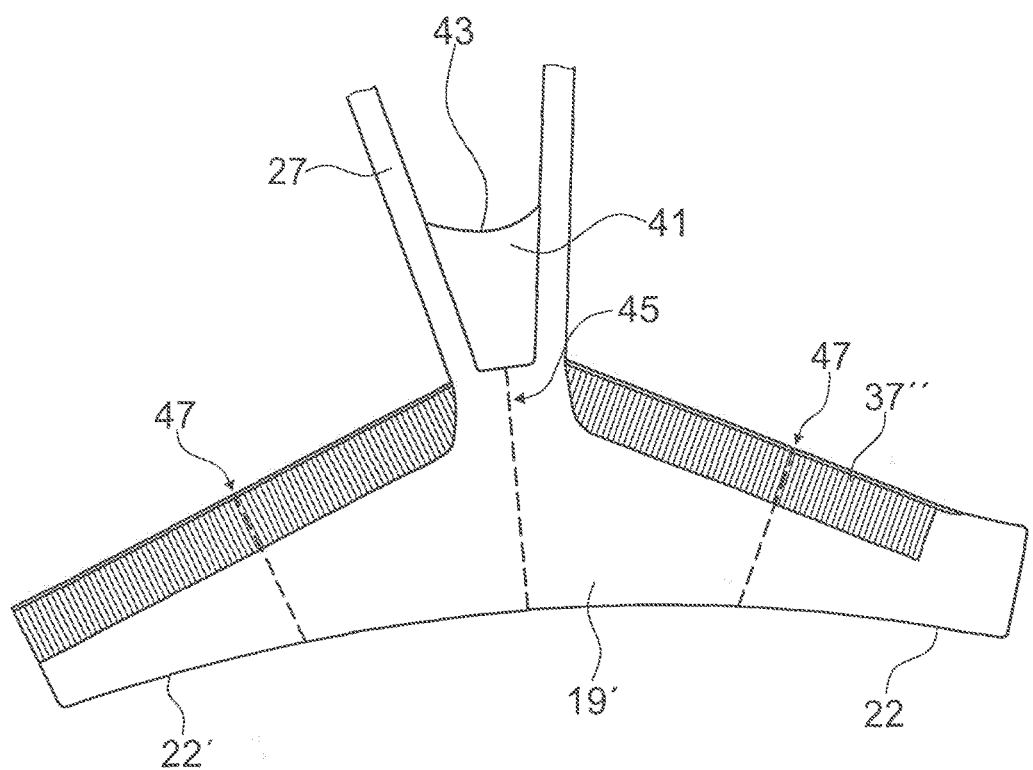
FIG. 4 shows an interior view of an inventive EIT belt with the support and attachment structure when stretched out.

In FIG. 4 it is visible that an optional stretchable and/or elastic cloth 41 is provided between the suspenders 27 of harness 19'. The cloth has an indentation 43, which can serve as indicator for the right positioning of the EIT belt. Indicators for indicating the midline 45 as well as further folding lines 47 are provided. This alleviates the positioning and dressing of the HIT belt to a bedridden patient. In this alternative harness design 19' the electrode band 16 is received in envelope 37", which is attached to the harness 19' along the upper rim of the straps 22, 22'.

Figure 5A:
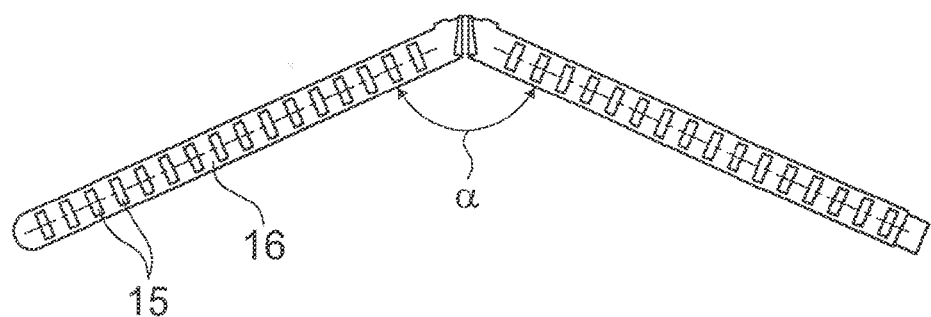
FIG. 5 shows a further embodiment of an EIT belt with the electrodes arranged along two angulated legs attached to a vest of stretchable material
 (a) an electrode band (i.e. a support structure with attached electrodes) alone,
 (b) an inside view of an electrode belt comprising an electrode band attached to a vest,
 (c) a partial front view of a closed EIT belt when wrapped around the thorax of a patient.
Figure 5B:
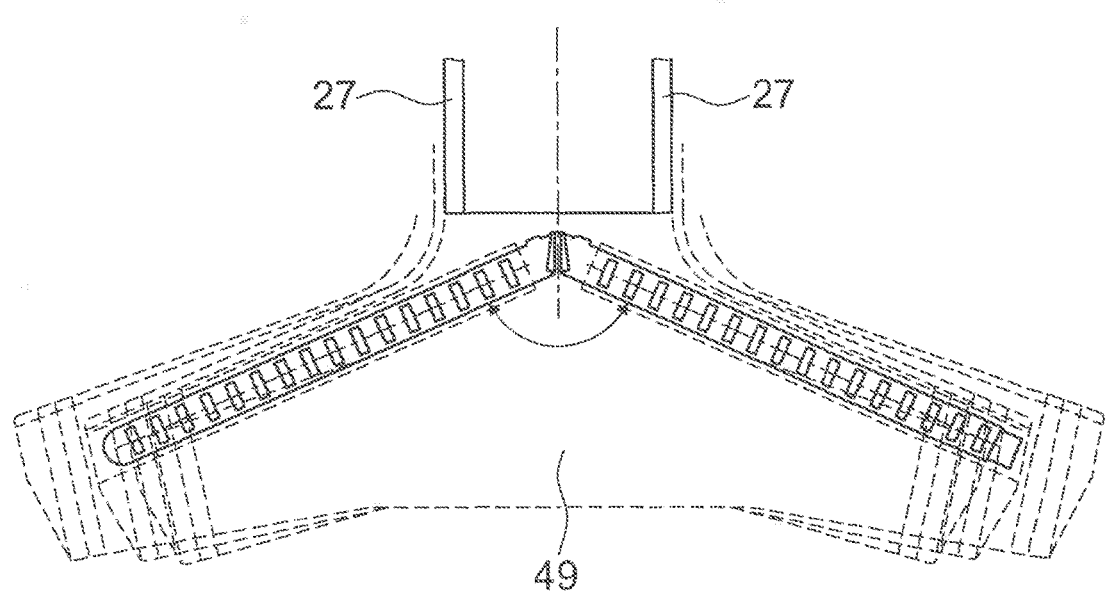
Figure 5C:
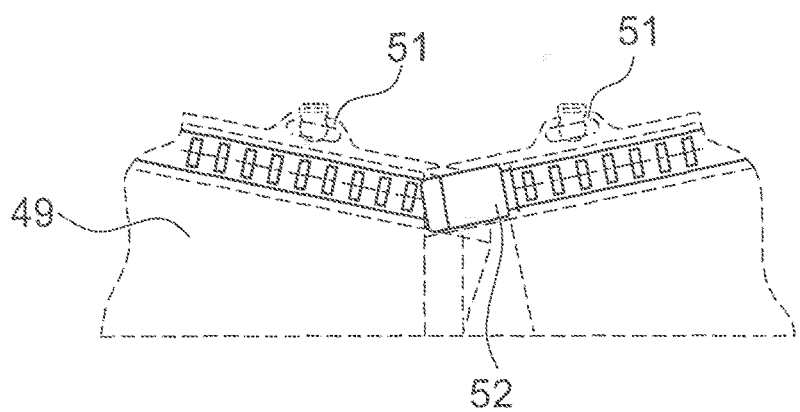

The embodiment of FIG. 5 distinguishes from that of FIG. 1 insofar as no middle part is provided so that the electrode band 16 is angulated in the middle so that the two legs of the band are separated by a bend. The angle α between the legs 31 can be in the range between 80° and 170°, between 90° and 160°, between 110° and 150°, or between 120° and 140°. FIG. 5a shows an angle a of exemplary 132 degrees. The electrode band 16 is attached to a vest 49, which is made of a stretchable material. The vest 49 (which is similar to the harness 19 or 19' of FIG. 1-4) has essentially the shape of a triangle whose lateral corners are cut off. FIG. 5b shows a vest 49 in differently stretched positions whereby the length of the electrode band 16 is unaltered. In FIG. 5b and FIG. 5c is depicted a connector 52 for connecting the electrode band to a control unit (not shown). FIG. 5c shows a vest with joined strap ends. At the same time the connector 52 connects the array of electrodes to a control unit, which further is connectable to a ET instrument. The vest 49 can be equipped with ears 51 through which the suspenders can be drawn.

Figure 6A:
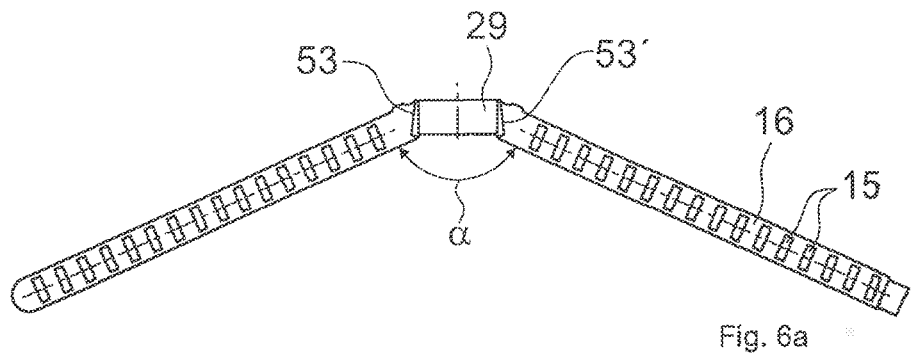
FIG. 6 shows a further embodiment of an EIT belt similar to that of FIG. 1 showing
 (a) the electrode band with a transverse part connecting the two angulated legs of support structure with attached electrodes alone,
 (b) an inside view of an electrode belt comprising an electrode band attached to a vest
 (c) a partial front view of a dosed EIT belt when wrapped around the thorax of a patient.
Figure 6B:
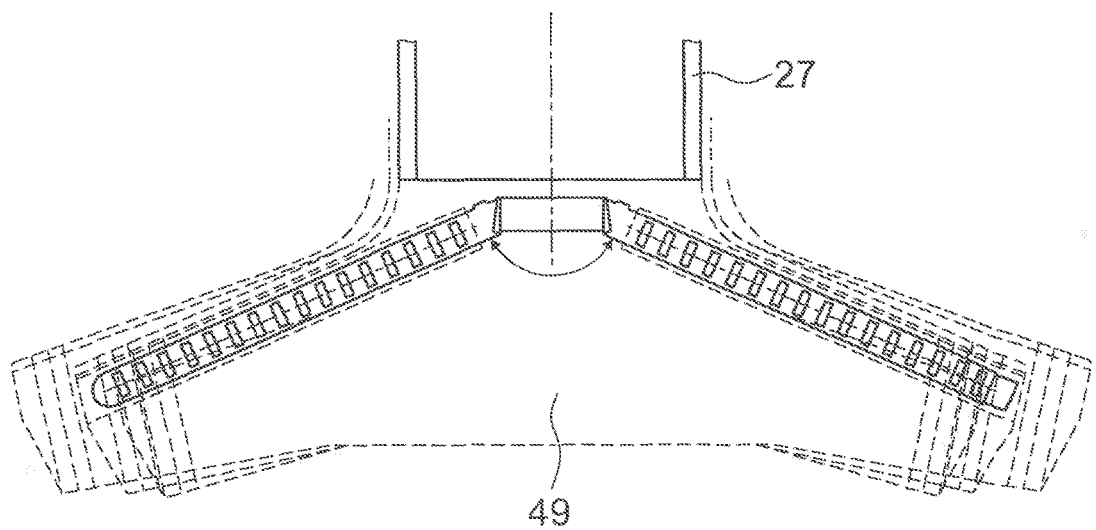
Figure 6C:
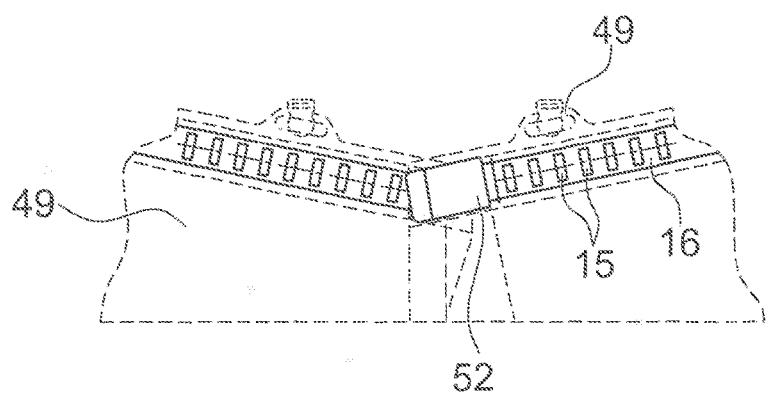

The embodiment of FIG. 6 is provided with a middle part 29 to which the legs 31 of the electrode band are hingedly connected. The provision of the middle part 29 has the advantage that the apex of the electrode band is at a lower position than with a configuration as shown in FIG. 5 so that the bends or hinges 53 and 53' are located behind the respective rib pints on both sides of the spinal column. This has the advantage that any movement of the belt is well coordinated with the movement of the ribs.

Figure 7:
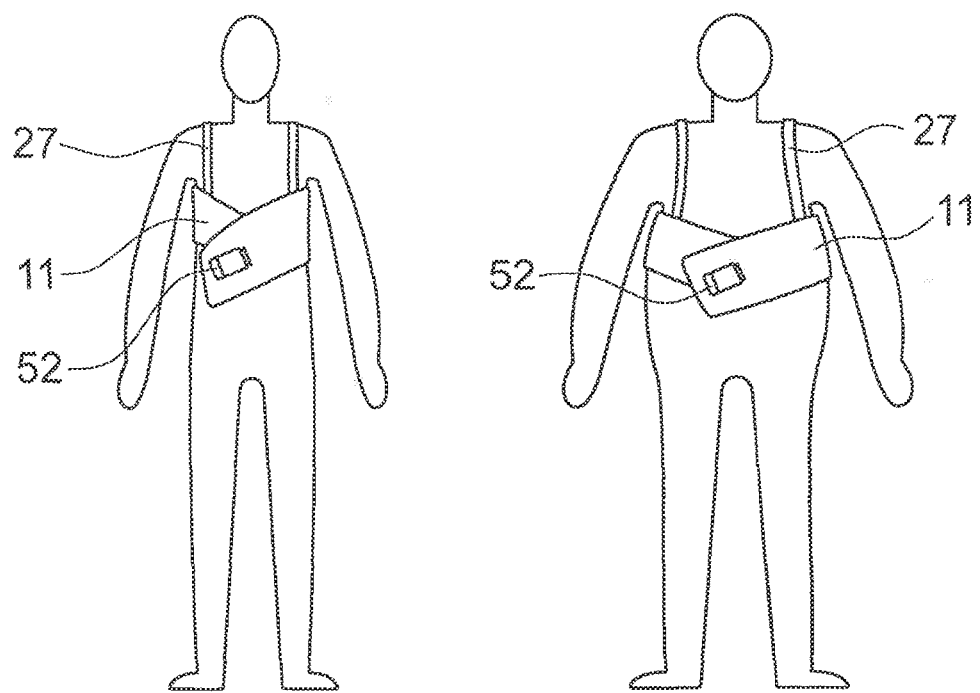
FIG. 7 shows two persons of different shape wearing an inventive EIT measuring belt.
Figure 8A:
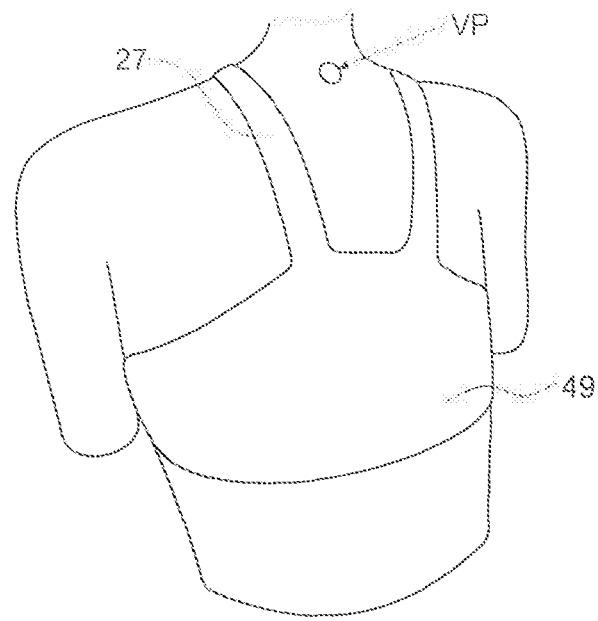
FIG. 8 shows a view of the hack of a patient carrying an inventive KIT measuring belt, (a) belt with suspenders and (b) vest-like belt.
Figure 8B:
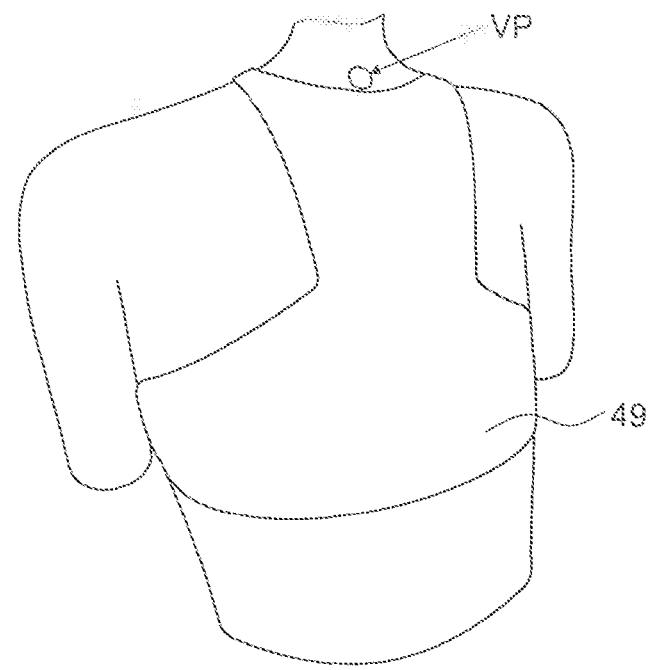
Figure 9:
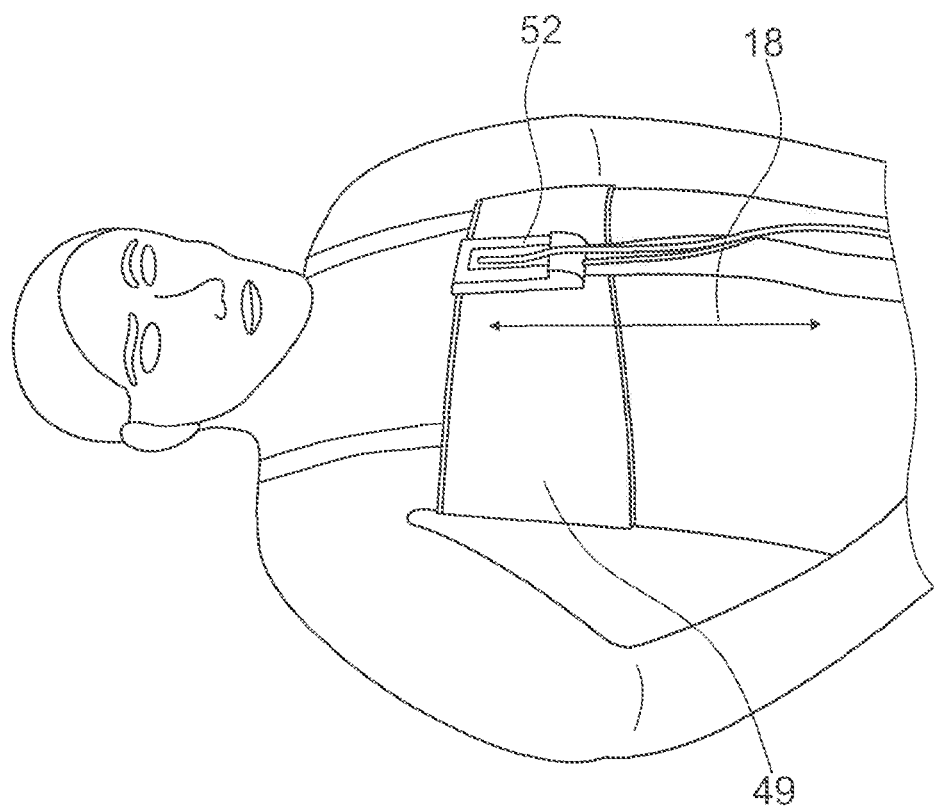
FIG. 9 shows a patient with the inventive EIT belt during EIT measurement.

FIG. 7 shows two persons with different physique being equipped with an inventive EIT measuring belt. In FIGS. 8 and 9 a test person is shown wearing a vest 49 equipped with an electrode band 16 (not visible here). At the neck, marker VP indicates the anatomic reference point of the vertebra prominens (C7). In FIG. 8a, advantageously, the electrode belt 49 is equipped with, suspenders. In FIG. 8b an exemplary vest-like electrode belt 49 is presented. At the neck portion, correct fitting of the belt may be verified in reference to marker VP. Connector 52 serves to establish contact between the array of electrodes and an EIT instrument.

Figure 10:
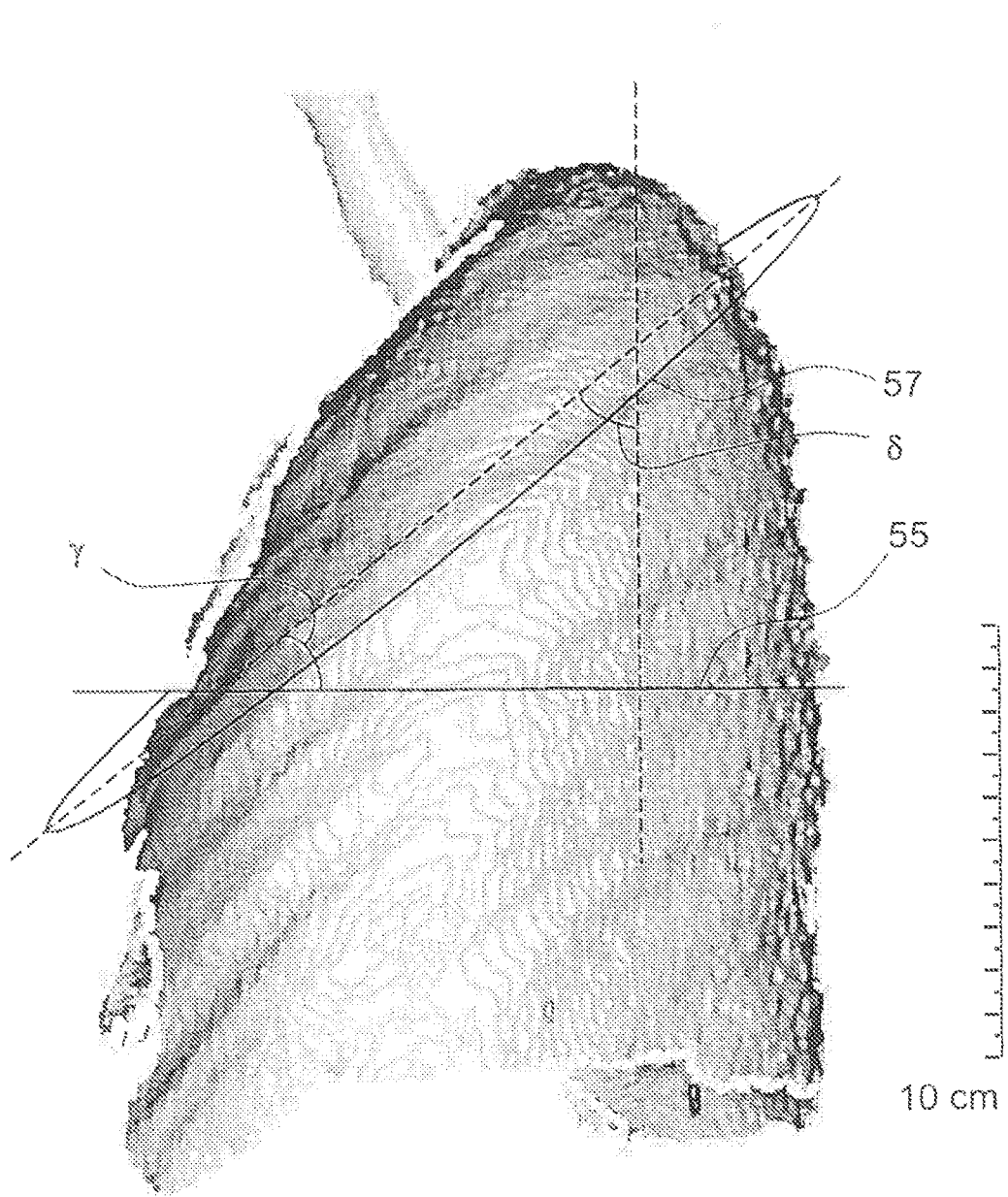
FIG. 10 shows a 3-D computer tomographic reconstruction of a healthy lung of a test person indicating the traditional transverse and the proposed new oblique electrode plane.

In FIG. 10 a computed tomography 3-D reconstruction (lateral view) of the lung of a test person is shown. The horizontal line 55 thereby illustrates the location of the traditional transverse electrode plane, which has been used so far for recording EIT images. The curved oblique line 57 illustrates the location of the novel oblique electrode plane proposed by the present inventors. The oblique oval electrode plane is at an angle γ with respect to the transverse plane (i.e. transverse body plane Angle γ with respect to the transverse plane approximately corresponds to the rib inclination with respect to the dorsoventral axis. Moreover, angle γ comprises approximately 20 to 60 degrees. Angle y determines angle δ between above mentioned transverse body plane and the longitudinal axis of the body following the relation γ+δ=90°.

Figure 11A:
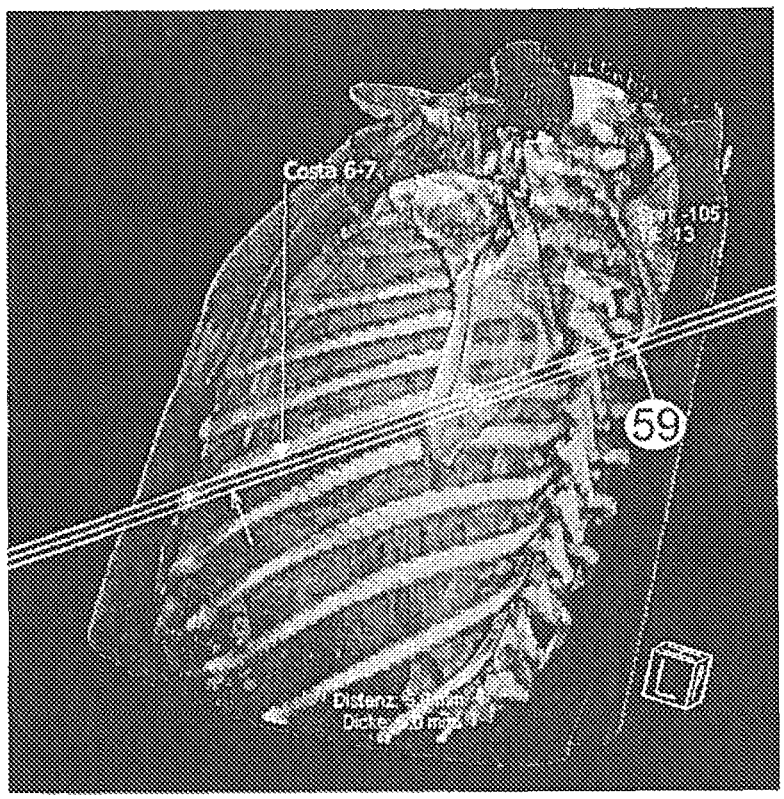
FIG. 11 shows (a) a 3D computed tomography representation of the heart and lung indicating conceptually the best position of the electrode array at the $6^{th}$ intercostal space, recording condition: distance 5.0 mm, thickness 5.0 mm; (b) tomographic 2D image obtained from an oblique cut through the 3D computed tomography representation at the $6^{th}$ intercostal space (i.e. oblique body plane between ribs 6 and 7).
Figure 11B:
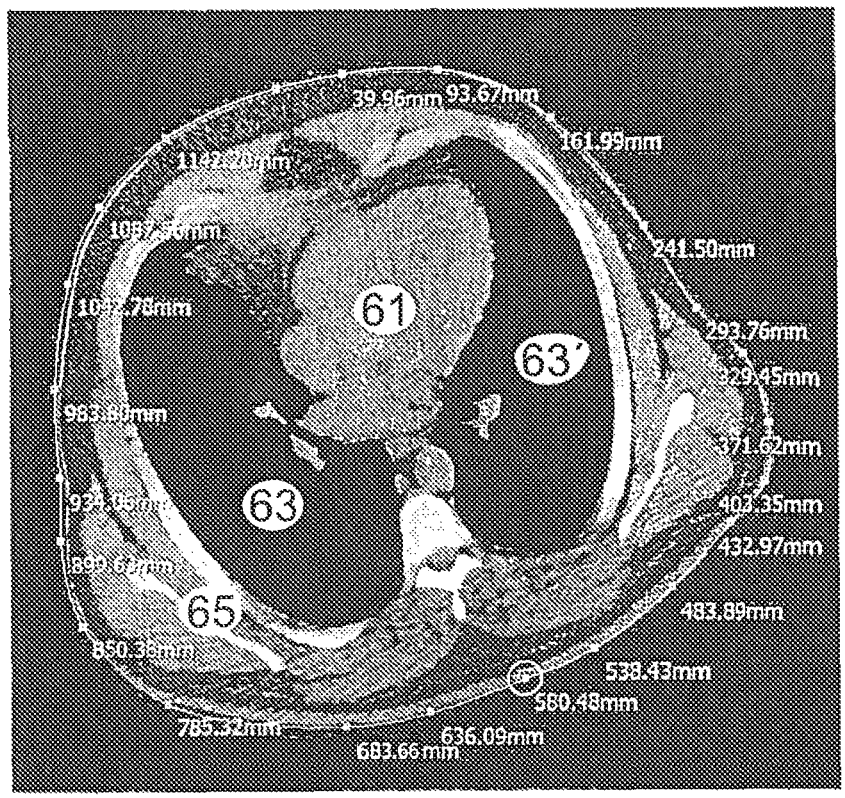

FIG. 11a shows a 3D computed tomography (CT) reconstruction images of a lung. The CT image presents the lung at a spin of −105 degrees and a tilt of 13 degree. FIG. 11b shows a computed tomography 2D image obtained from an oblique cut through the 3D CT scan of FIG. 11a at an angle as indicated by triple line 59 at the 6$^{th}$ intercostal space. One can recognize in the upper middle the heart 61, which is surrounded on both sides by the lung 63 and 63' within the thorax 65. The body plane circumscribed by the 6$^{th}$ intercostal space on both sides of the thorax as indicated by line 59 shows a wide area of lung and heart tissue. An EIT image at this position therefore allows a representative determination of heart and lung conditions of a patient.

In the following further details or advantageous features of the EIT measuring belt are summarized:

The electrode belt may be designed as a stretchable or a non-stretchable type belt. The non-stretchable belt type is desired. For closing the two overlapping ends of the belt a VELCRO hook and loop fastener closing is proposed although any other appropriate closing means could be used. In particular, the support structure 13 is non-stretchable (thus the electrode band 16 is non-stretchable), while the attachment structure 19, 19' or 49 may or may not be stretchable.

The vest comprises slots, in particular vertical slots, or other fixation means for attaching the electrode band or support structure. These slots may be formed by cutting parallel slot pairs into the vest material. Each slot pair functions as a fastener or loop for accommodating and holding a belt-like support structure or electrode band. Alternatively, a thread may be affixed to the vest or other attachment device forming a strap or loop. Further alternative fixation means are push-buttons, VELCRO hook and loop fasteners or other means (e.g. glue or adhesive tape) resulting in a fixed connection of electrode band and vest-like garment.

The vest-like garment comprises at least one fixation point with a fastener such as a loop 35 or VELCRO hook and loop fastener, or several such fixation points, such as 2 to 8 fixation points.

At one or both of the elongate ends of the vest, for holding the ends of the electrode band, the vest material may be folded back to form a pocket for enclosing the ends of electrode band.

The fasteners or loops of the fixation point hold the support structure and, therefore the electrode array in place. Pre-fabricated folds prevent the electrode band from shifting and inhibit the blocking of sensors.

There is a strict distinction (and physical separation) between the functional belt-like support structure carrying the EIT electronics (electrode band) and the textile attachment structure or vest-like garment. The vest-like garment is merely considered an attachment means to fix such belt-like support structure on the patient's body.

Figure 2:
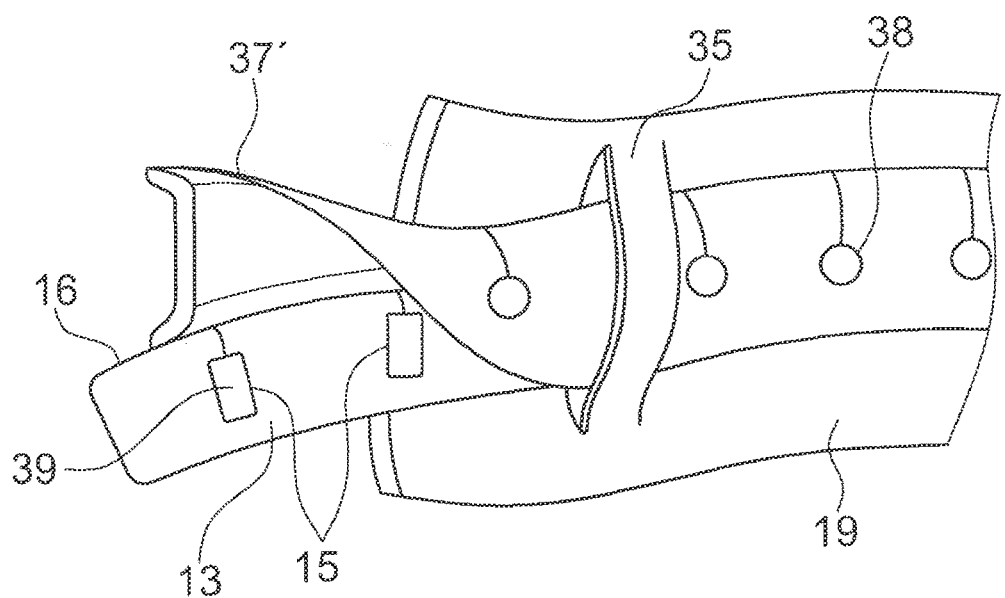
FIG. 2 shows a support structure with electrodes and an interface in the form of an electrically conductive textile in a sandwich-like structure with a permanent contact to the support structure.
Figure 3:
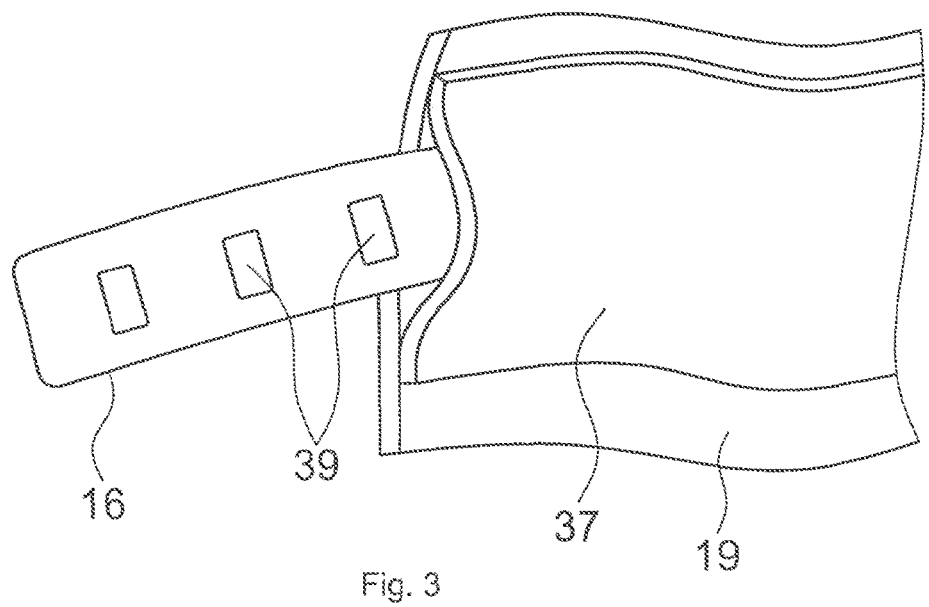
FIG. 3 shows a support structure with electrodes being placed in a tube-like conductive textile, which can be an integral part of the attachment structure or a vest-like harness.

The electronics are provided in a belt-like sandwich structure as shown in FIG. 2 or in a tube-like fashion as shown in FIG. 3. The belt-like sandwich structure, comprises a married relation between electronics and conductive material. In particular, it is a sandwich of electronic belt (i.e. support structure with electrodes) and soft padding together with conductive material (FIG. 2). The soft padding of the tubular structure 37' comprises conductive lines 38 which serve as an electrode-to-skin contacting means.

While a tubular structure 37 comprises a married relation between an electrically conductive material and the attachment structure or vest 19 (FIG. 3), a soft spacer fabric with integrated conductive pathways or such pathways extending around it creates a tube-like pocket for holding the support structure carrying the electrode sensors and at the same time connecting the electrode sensors electrically to a body, i.e. to skin.

Where body surface area is covered, by the vest-like support in order to reliably fix the EIT electrode sensors on the body, it is desirable to use appropriate skin-friendly materials.

Further it is desirable that the belt is adapted to be opened and closed easily and also multiple times (possibly 5-10 times a day}, e.g. for patient care, medical examination or patient transport.

It has been found that a sufficiently wide area of materials at the caudal edge of the belt should be provided in order to: Firstly, keep the sensors in place and to secondly, prevent the electrode bands ventral portion from moving cranially. This can best be achieved by a vest or vest-like harness. A respective downward/caudal movement is prevented by appropriate shoulder straps or suspenders.

For manufacturing the vest an appropriately thin textile material is desired, so that auscultation could even be performed through the vest material without having; to remove it for such examination. A thin breathable textile or non-woven material does qualify for such use.

The presence of chest tubes in some patients can be taken into account for the vest layout. However, due to the fact that: the vest may be a disposable for single patient use, simple holes or cuts could easily be performed or applied according to the individual patients needs, provided the material does not disintegrate in the presence of thereby inflicted discontinuities.

The vest material in contact with the skin has one or more of the following characteristics:
  disposable (ideally recyclable or with the least environmental impact);
  breathable;
  as thin as reasonably possible;
  materials directly touching the skin should not cause its irritation or allergic sensitization, but rather act like a second skin (see respective standards on biocompatibility);
  elasticity should, ideally be spread all over the material and not confined to specific (small) areas thereby imitating a second skin in the best possible way;
  repellent for water, body fluids and dirt;
  vest material should not cause artifacts in the patients' CT images so that the belt can be worn even during CT exams; and/or
  in order to ensure best possible fit (like a "second skin") vests can be delivered in different sizes.

In order to facilitate usage and application of the vest, markers or "help lines" may be provided, such as e.g. the following:
  at the site of closure to indicate the exact current closing position e.g. of a VELCRO hook and loop fastener closing, to facilitate adjustment, re-positioning or re-closure by such visual clues,
  an indicator of a midline (to run along the patient's spine),
  a physical marker of the distance to points of anatomic reference, such as e.g. the "vertebra prominens" (C7) ("Sports-Bra-Design"),
  lines indicating the best position for folding the vest during application on both sides, and/or
  indication and numbering of electrodes at their respective positions shall ideally be provided on the surface of the vest so as to allow to draw inferences from the electrode numbers as shown on the display of the medical device to the anatomical location of such (potentially failing) electrodes.

A docking station (e.g. a connector 52) can be placed on the EIT measuring belt at a position, which is at the front of a patient, i.e. on the patient's chest, when wearing the belt. The belt connector plug (and its docking station) is aligned with the patient's longitudinal axis (FIG. 9). The docking station of the belt connector is tightly fixed to the vest to facilitate handling. An automatic click-fix system might be desirable.

While the invention has been described above with reference to specific embodiments thereof, it is apparent that many changes, modifications, and variations can be made without departing from their inventive concept disclosed herein. Accordingly, it is intended to embrace all such changes, modifications and variations that fall within the spirit and broad scope of the appended claims.

What is claimed is:

1. An electro impedance measuring system, comprising:
    a belt for placing electrodes around the thorax of a patient, the belt comprising;
    an electrode array comprising a plurality of spaced apart electrodes for electro impedance imaging; and
    a support structure comprising a belt, on which the electrode array is arranged, having two angulated legs on which the plurality of spaced apart electrodes are aligned, the two angulated legs spread out from an apex of the support structure at a first angle, such that, when the belt is placed around a thorax of a patient, the electrode array and the two angulated legs of the support structure extend from a back of the patient with the apex of the support structure located over a thoracic vertebrae of the patient, the two angulated legs of the support structure each extending downward from the apex in an opposite direction to one another and wrapping around the thorax to the front of the patient and over a lower part of a breastbone of the patient, the electrode array having a first portion extending along a first of the two angulated legs from proximate the apex of the support structure around the thorax of the patient to proximate the lower part of the breastbone of the patient and a second portion extending along a second of the two angulated legs from proximate the apex of the support structure around an opposite side of the thorax of the patient to proximate the lower part of the breastbone of the patient, the first and second portions of the electrode array positioned substantially parallel to the patient's ribs; and a processor configured for electro impedance imaging coupled to the electrode array.

2. The system of claim 1, wherein the first angle formed between the legs is between 80 and 170 degrees.

3. The system of claim 1, wherein the legs are connected by a transverse middle part and wherein a second angle between a longitudinal axis of the middle part and a longitudinal axis of each leg is between 15 and 35 degrees.

4. The system of claim 1, wherein the legs comprise an electrode band, and further comprising a first fastener proximate a first end and second end of the electrode band for connecting the first and second ends together.

5. The system of claim 1, further comprising an attachment structure for holding the support structure and the array of electrodes in position relative to a patient so that relative movement of the electrodes and a body of the patient is substantially limited during breathing.

6. The system of claim 5, wherein the attachment structure is configured to be coupled to the body of the patient and also to the support structure.

7. The system of claim 5, wherein the attachment structure comprises a harness configured to hold the support structure in position.

8. The system of claim 7, wherein the harness comprises a vest-like structure configured to position and carry the support structure and the electrode array.

9. The system of claim 8, wherein the vest-like structure is comprised at least partially from an elastic textile.

10. The system of claim 5, wherein the attachment structure and the support structure are releasably connected to each other.

11. The system of claim 5, wherein the electrode array when coupled to the attachment structure and spread out flat has a generally curved V shape for aligning with a rib inclination of the patient.

12. The system of claim 1, wherein the electrode array and the support structure are integrally formed and comprise at least two layers including a first layer comprising a skin-contacting cloth with electrically conducting pathways for establishing contact between the skin and the electrodes, and a second layer comprising an electronic circuit board.

13. The system of claim 12, wherein the support structure defines a plurality of electrode positions, and further comprising at least one of supply lines, control lines and data lines to connect the electrode array with analyzing and control equipment.

14. The system of claim 1, wherein the support structure comprises a non-stretchable and non-elastic material including a circuit board.

15. The system of claim 1, wherein the belt is configured for a single use.

16. The system of claim 1, wherein the array of electrodes define an oblique oval plane at an angle with respect to a transverse plane due to inclination about a transverse axis running from a left to a right side of a body of the patient.

17. The system of claim 16, wherein the angle approximately corresponds to a rib inclination with respect to a dorsoventral axis.

18. The system of claim 1, wherein the array of electrodes extend along one specific rib on one side of a body of the patient and a corresponding specific rib on an opposite side of the body.

19. The system of claim 1, wherein the array of electrodes extend between a 4th and a 7th rib of the patient.

20. The system of claim 19, wherein the array of electrodes is positioned at a level of a specific intercostal space of the ribs of the patient.

* * * * *